United States Patent [19]

Noiles

[11] 4,299,224

[45] Nov. 10, 1981

[54] DISPOSABLE CLIP APPLIER

[75] Inventor: Douglas G. Noiles, New Caanan, Conn.

[73] Assignee: United States Surgical Corporation, Norwalk, Conn.

[21] Appl. No.: 46,185

[22] Filed: Jun. 6, 1979

[51] Int. Cl.³ .................. A61B 17/12; A61B 17/04; B31B 1/00

[52] U.S. Cl. ........................ 128/325; 128/334 R; 227/19; 227/DIG. 1

[58] Field of Search ............. 128/354, 321, 322, 325, 128/326, 340, 346; 227/19, DIG. 1, 243.56; 29/816

[56] References Cited

U.S. PATENT DOCUMENTS

| | | | |
|---|---|---|---|
| 2,455,833 | 12/1948 | Trombetta | 128/326 |
| 2,549,731 | 4/1951 | Wattley | 128/354 |
| 2,968,041 | 1/1961 | Skold | 1/49.1 |
| 3,232,089 | 2/1966 | Samuels et al. | 72/410 |
| 3,777,538 | 12/1973 | Weatherly et al. | 72/410 |
| 3,827,277 | 8/1974 | Weston | 128/326 |
| 3,871,379 | 3/1975 | Clarke | 128/326 |
| 4,050,465 | 9/1977 | Périssé | 128/326 |
| 4,152,920 | 5/1979 | Green | 72/410 |

FOREIGN PATENT DOCUMENTS 393010  6/1933  United Kingdom .............. 128/326

*Primary Examiner*—Robert W. Michell
*Assistant Examiner*—C. W. Shedd
*Attorney, Agent, or Firm*—Fleit & Jacobson

[57] ABSTRACT

A disposable instrument for applying surgical clips consisting of a clip applier and a cartridge mounted thereon. The instrument consists of a housing having a body portion and an elongated sleeve portion extending from the front of the body portion. Disposed for rectilinear movement within the sleeve and body portions is a jaw blade which terminates at its free end in a pair of opposed clinching jaws resiliently spaced apart. The jaw blade is slidably mounted in the housing and coacts with a portion of the housing structure for closing the clinching jaws together, the movement of the jaw blade defining a first plane. Positioned within the housing for arcuate movement are a pair of handles, the movement of the handles defining a second plane. A pair of links provides a force-transferring connection between the handles and the jaw blade. Each handle defines a force-imparting cylindrical surface the axis of which is substantially perpendicular to the plane defined by the movement of the handles. Each of the links contains a cylindrical peripheral edge portion that defines a force-receiving surface, the axis of which is substantially perpendicular to the plane defined by the movement of the jaw blade. In operation, when the handles are moved toward each other, the force-imparting surface bears against the force-receiving surface to facilitate movement of the jaw blade in order to accomplish a clinching of the clip disposed between the jaws.

A clip cartridge is slidably affixed to the sleeve portion of the clip applier. The clip cartridge is movable towards and away from the clinching jaws of the clip applier so that a number of surgical clips can quickly and successively be supplied to the clinching jaws.

26 Claims, 19 Drawing Figures

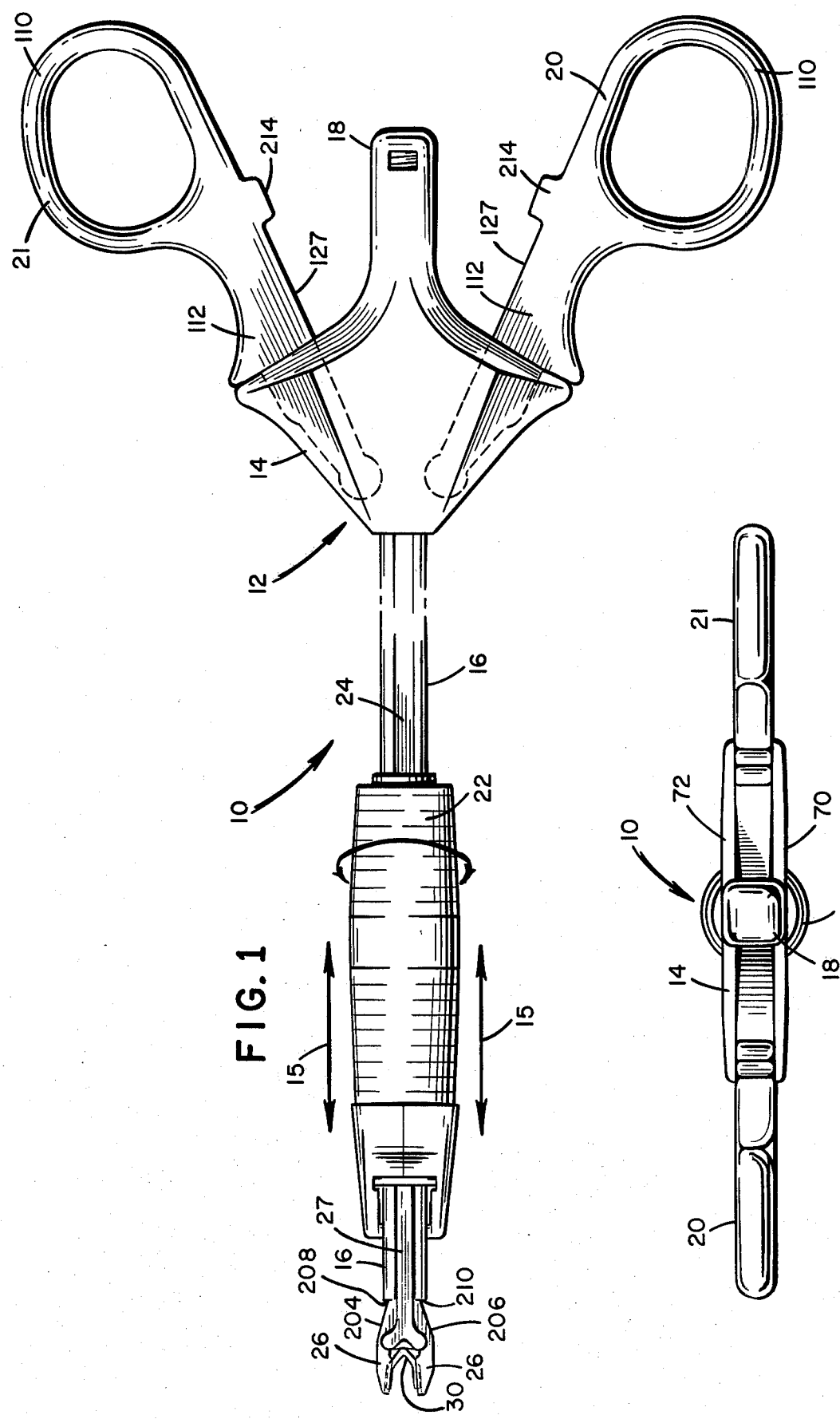

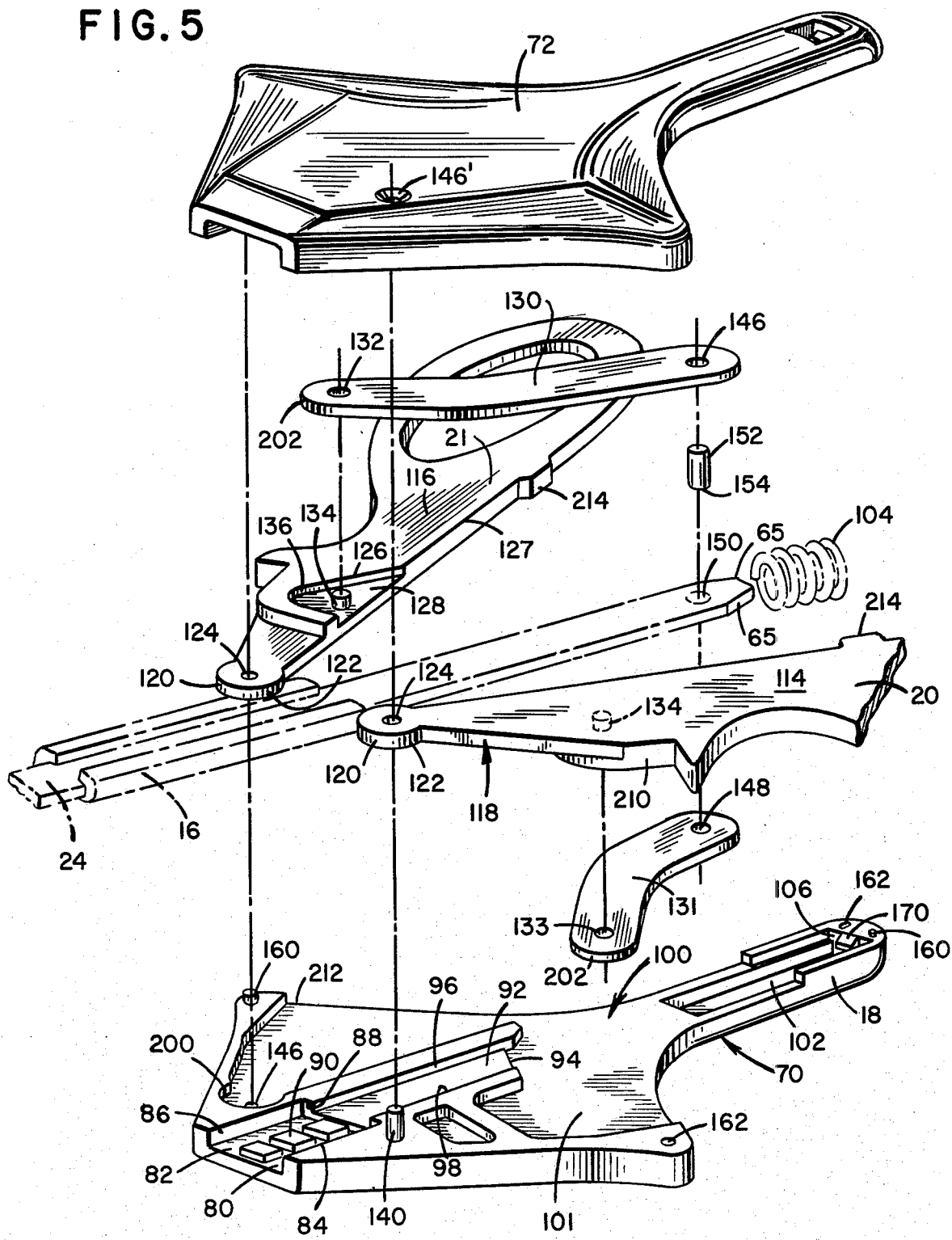

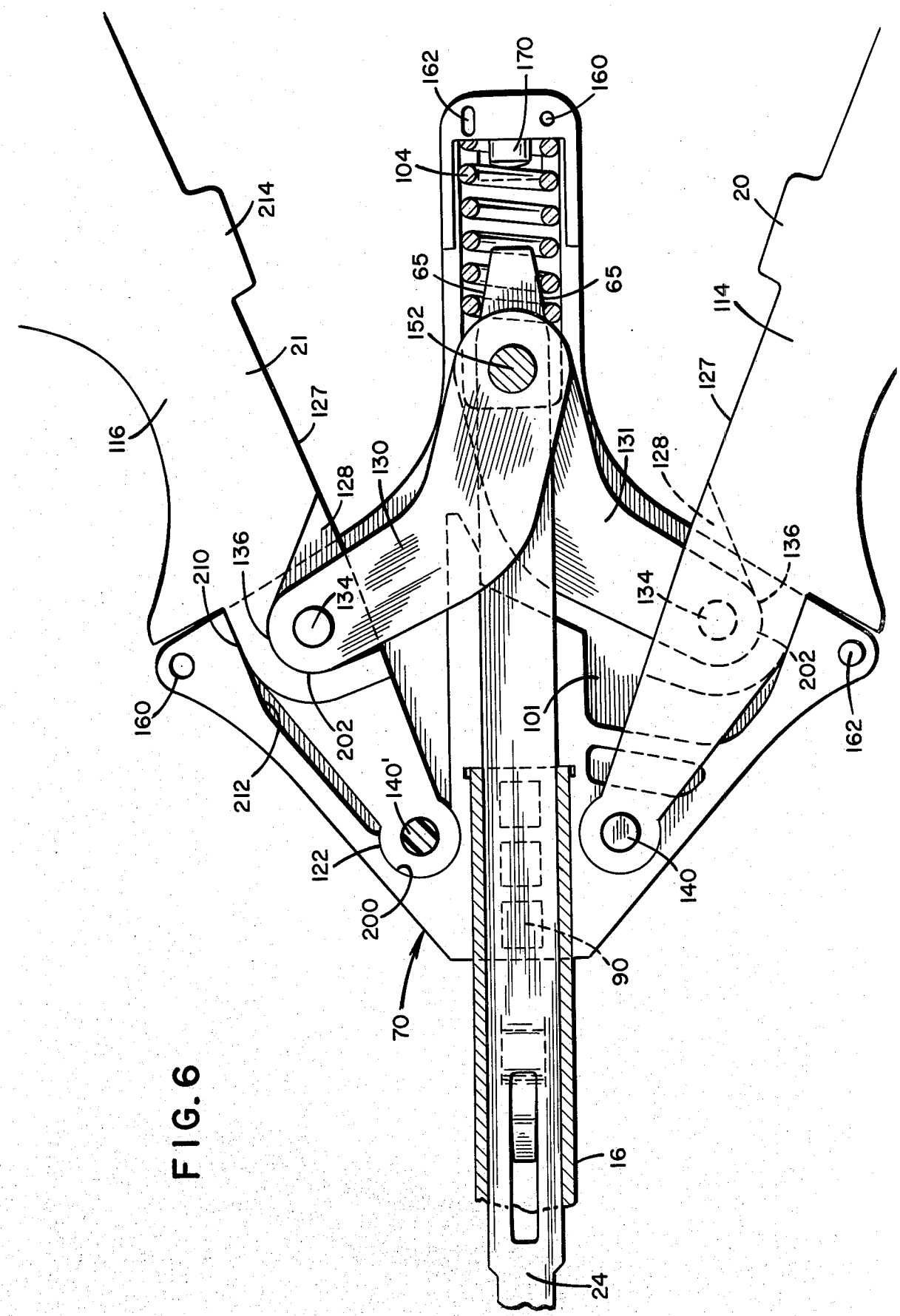

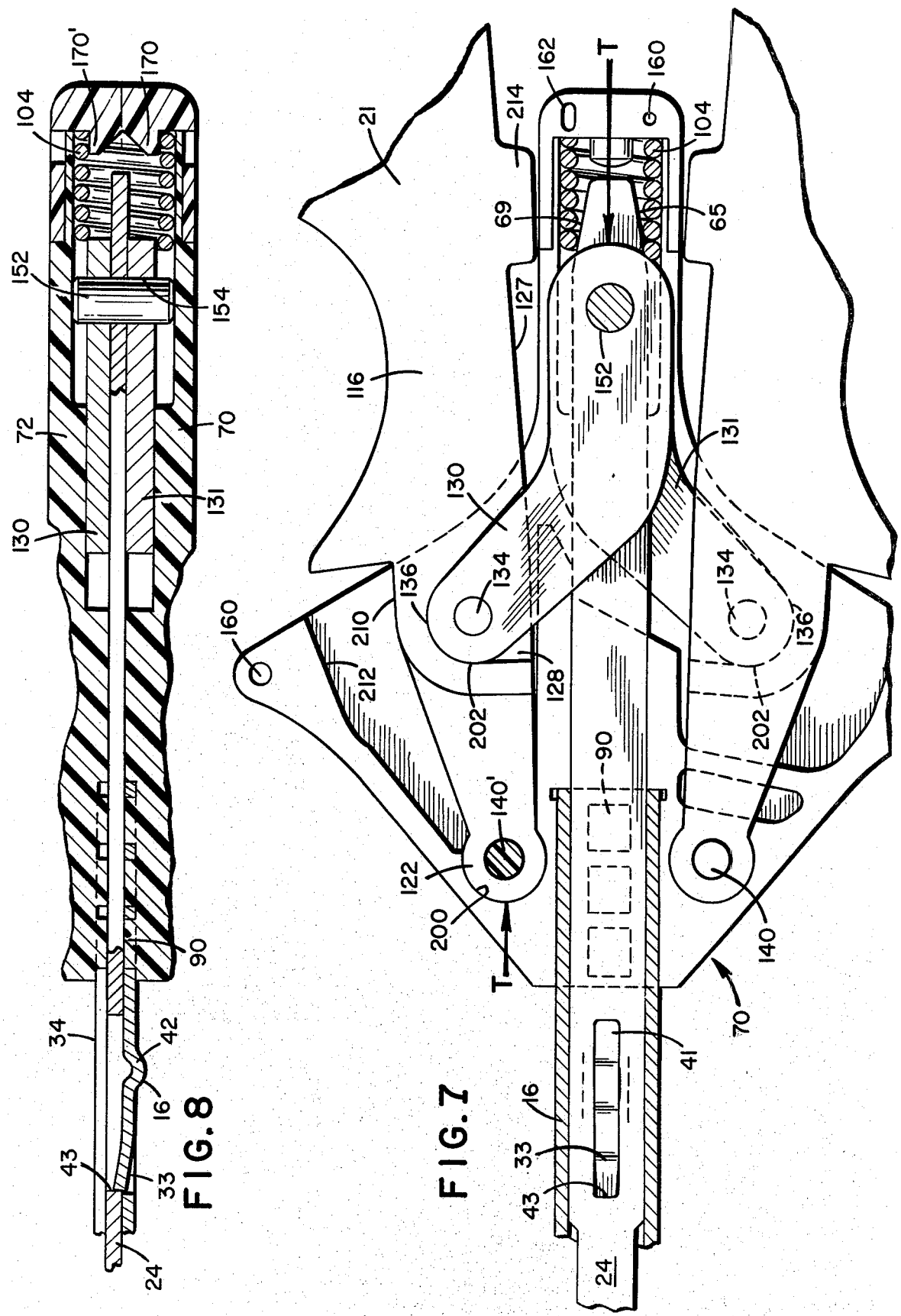

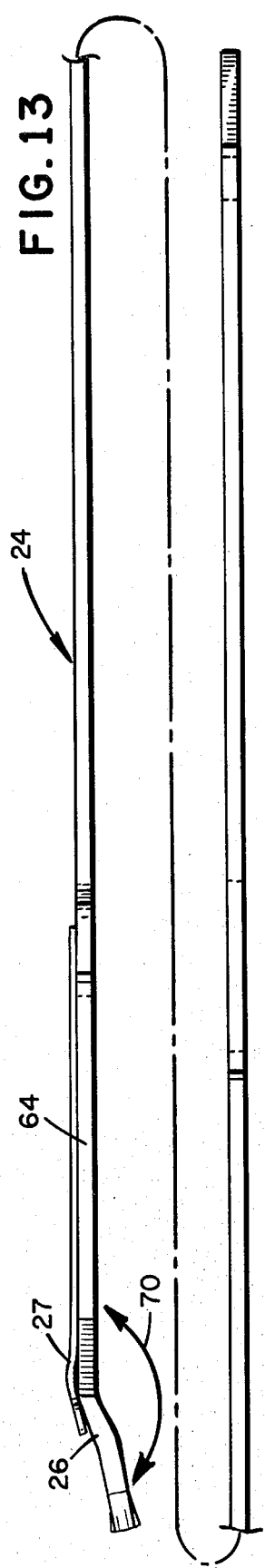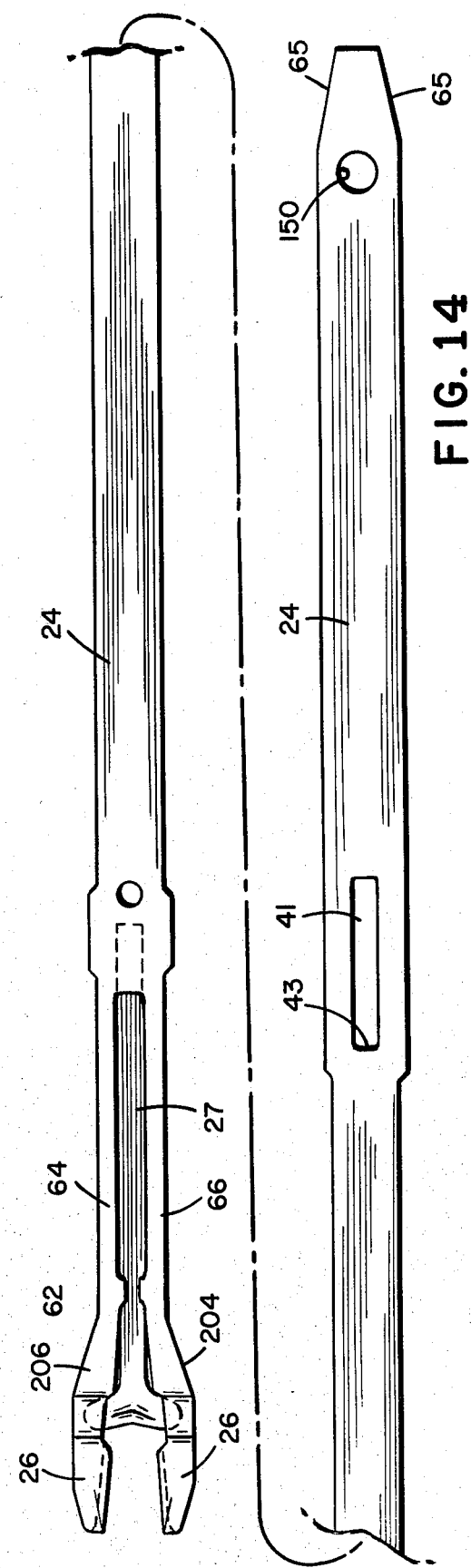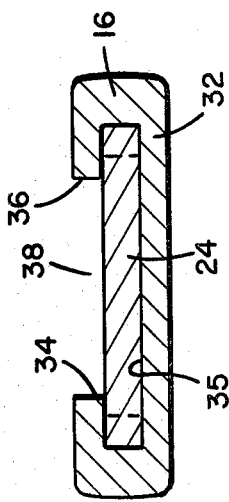

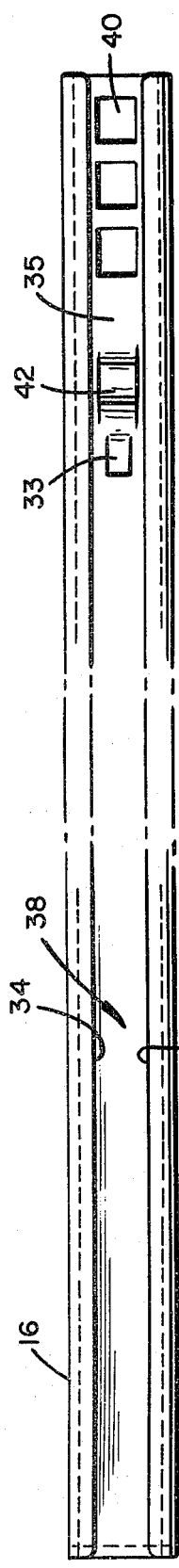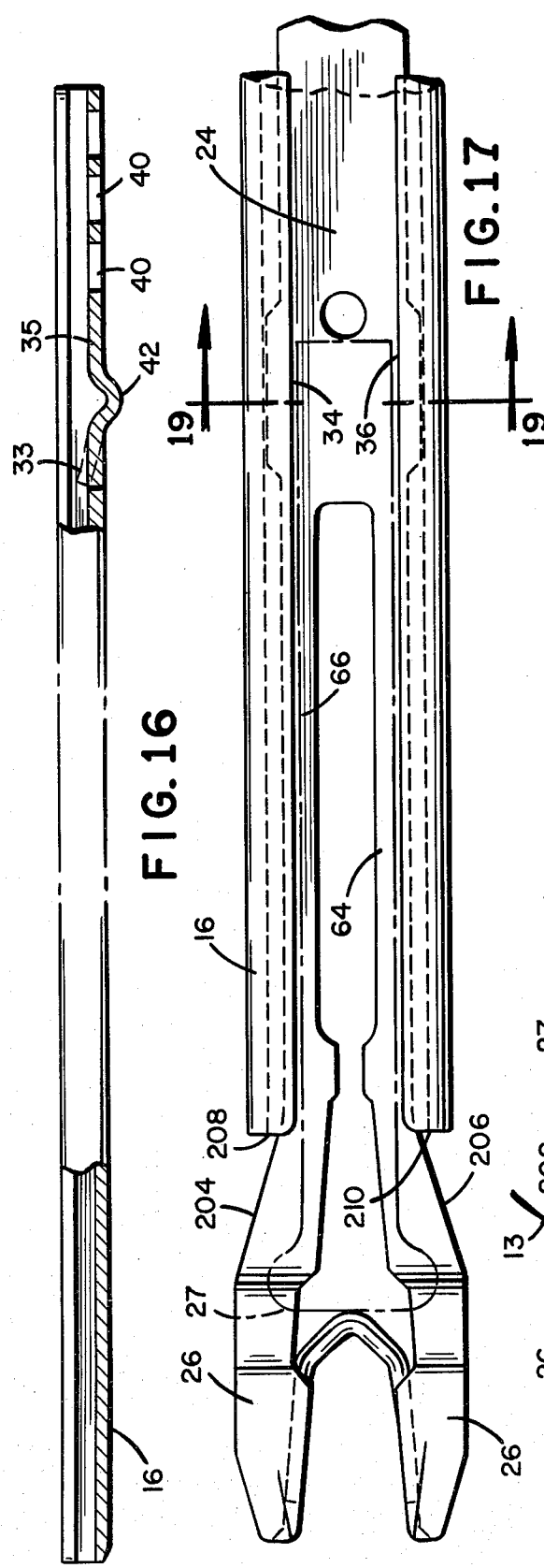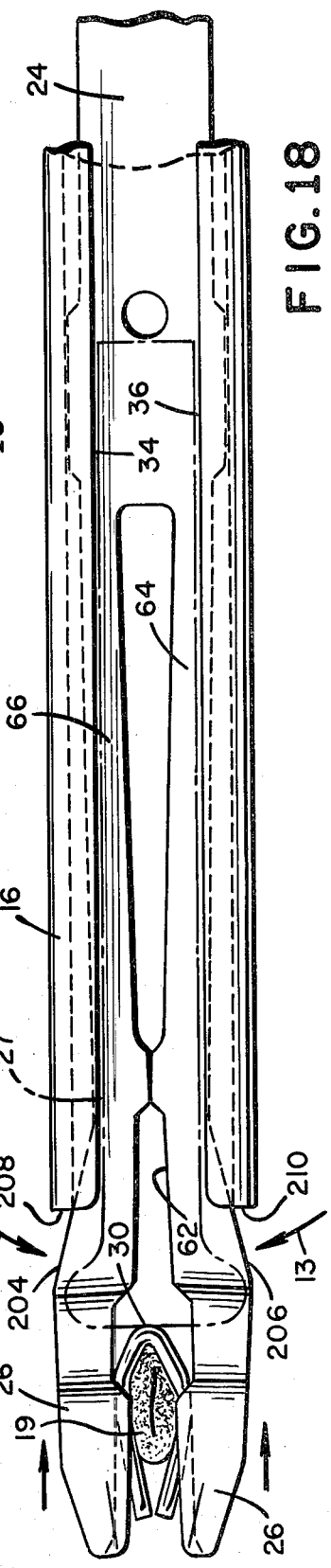

DISPOSABLE CLIP APPLIER

BACKGROUND OF THE INVENTION

1. Field of the Invention

This invention relates to a surgical instrument, in general, and to a disposable surgical device for applying surgical clips to blood vessels or other body tissue, in particular.

2. Description of the Prior Art

In recent years, there have been proposed a number of surgical clip applicators for applying a clip to a blood vessel or the like. These instruments include an auxiliary cartridge or magazine capable of holding a sufficient number of surgical clips to accommodate the vessel-restricting requirements of most surgical procedures and of releasing clips, one at a time, successively as required. Specific examples of surgical instruments which utilize or include a cartridge or magazine are disclosed in U.S. Pat. Nos. 2,968,041; 3,232,089 and 3,777,538. The advantages of applicators of this type are enumerated at length in the specifications of the three patents just mentioned.

Until recently, the prior art did not suggest a system for applying surgical clips which incorporates a disposable cartridge detachably mounted on a permanent instrument. In this regard, two particularly advantageous surgical applicators of the magazine or cartidge type are disclosed in U.S. Pat. No. 4,152,920 issued May 8, 1979, and copending U.S. patent application Ser. No. 905,030, filed May 11, 1978.

Basically, all of the instruments mentioned above include a pair of movable jaws between which a clip is held preparatory to clinching. The jaws are drawn toward each other in response to a manual force applied by a surgeon to a handle arrangement operatively associated with the jaws by way of an actuator. In all of the known instruments, the parts which work in concert to accomplish application of a surgical clip are made entirely of metal, typically stainless steel. This is because a substantial force and mechanical advantage must be developed, through manual manipulation of the movable parts of the handle arrangement, in order to close the jaws to perform a clinching of the clip. As such, the structural designs of the prior art instruments do not readily lend themselves to the production of a fully disposable clip applier with an integral cartridge or magazine.

There is thus a need for a fully disposable clip applier which may be economically manufactured and which is capable of developing the substantial force and mechanical advantage necessary to perform a proper clip application in response to a manually applied force no greater than that force applied to actuate any of the prior art instruments. The present invention is directed toward filling that need.

SUMMARY OF THE INVENTION

Since plastic is a material which can be easily and economically molded, extruded, or cast into various parts, it readily lends itself to the production of disposable surgical instruments. Heretofore, it has not been possible to produce a reliable disposable clip applier made predominately of plastic, primarily because of the limited strength of plastic parts and the requirement that a substantial force and mechanical advantage be developed through manual actuation of the handles in order to close the jaws, and thereby accomplish a clinching of the clip.

The present invention takes into account the strength limitations of plastic parts and the force requirements taught by the prior art metal devices to produce a disposable surgical device for applying, one at a time, a number of clips, which are stored in a cartridge that is an integral part of the device.

A device, produced according to the teachings of the present invention, includes a housing having a plastic body portion and an elongated metal sleeve portion extending from the front of the body. An elongated metal jaw blade, slidably mounted in the sleeve for bi-directional movement in one direction and the opposite, has at its free end, a pair of opposed clinching jaws resiliently spaced apart. A pair of plastic ring handles, movably mounted in the body, travel toward each other in response to a manually applied force. The force developed by the arcuate movement of the handles is transferred to the jaw blade by a pair of links. The jaw blade, in response, moves into the housing and cooperates with a portion of the sleeve structure to accomplish a closing of the jaws and a clinching of a surgical clip disposed between the jaws.

A clip cartridge, having a plastic housing, is slidably affixed to the sleeve portion of the inventive clip applier. The clip cartridge is movable towards and away from the clinching jaws of the clip applier so that a number of surgical clips can quickly and successively be supplied to the clinching jaws.

In use, the rectilinear movement of the jaw blade within the housing defines a first plane, while the arcuate movement of the ring handles defines a second plane. In a preferred embodiment of the clip applier, the first and second planes are parallel to each other. Formed on each of the handles is a socket as defined by a force-imparting cylindrical surface the axis of which is substantially perpendicular to the second plane. The force developed by the arcuate movement of the handles is transferred to the jaw blade by a pair of links, each of which contains a peripheral edge portion that defines a force-receiving surface that is substantially perpendicular to the first plane defined by the movement of the jaw blade. Each of the links is received in one of the sockets in the manner of a hinge.

In order to develop the mechanical advantage necessary to move the jaws towards each other, the force-imparting surfaces bear against the force-receiving surfaces, when the handles are manually moved toward each other, to facilitate movement of the jaw blade in order to perform a clinching of the clip disposed between the jaws.

Thus, it is an object of the present invention to provide a disposable surgical device for applying a clip to a blood vessel or other body tissue.

It is another object of the present invention to provide a disposable clip applier which incorporates a clip magazine or cartridge for quickly and successively supplying clips to the clinching jaws of the device.

It is yet another object of the present invention to provide a disposable surgical device, whose design takes into account the strength limitations of plastic materials.

It is still an object of the present invention to provide a disposable surgical device which is structurally simple and economical to manufacture.

It is a further object of the present invention to provide a clip applier made predominately of plastic and capable of developing the substantial force and mechanical advantage necessary to perform a proper clip application.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 1 is a top plan view of a disposable clip applier.
FIG. 4 is a rear view of the clip applier.
FIG. 5 is an exploded view of the clip applier.
FIG. 6 is a plan view with the top body part removed. The handles are opened and the sleeve is in section.
FIG. 7 is a plan view similar to FIG. 6 except the handles are closed.
FIG. 8 is longitudinal section through the body of the clip applier.
FIG. 13 is a side elevation of the jaw blade of the clip applier.
FIG. 14 is a bottom plan view of the jaw blade of FIG. 13.
FIG. 15 is a top plan view of the sleeve of the clip applier.
FIG. 16 is a side elevation, partly in section, of the sleeve of FIG. 15.
FIG. 17 is a top plan view of the sleeve and jaw blade with the clinching jaws opened.
FIG. 18 is a top plan view of the sleeve and jaw blade with the clinching jaws closed.
FIG. 19 is a cross-section as viewed along line 19—19 of FIG. 17.

DETAILED DESCRIPTION OF THE DRAWINGS

Figure 3:
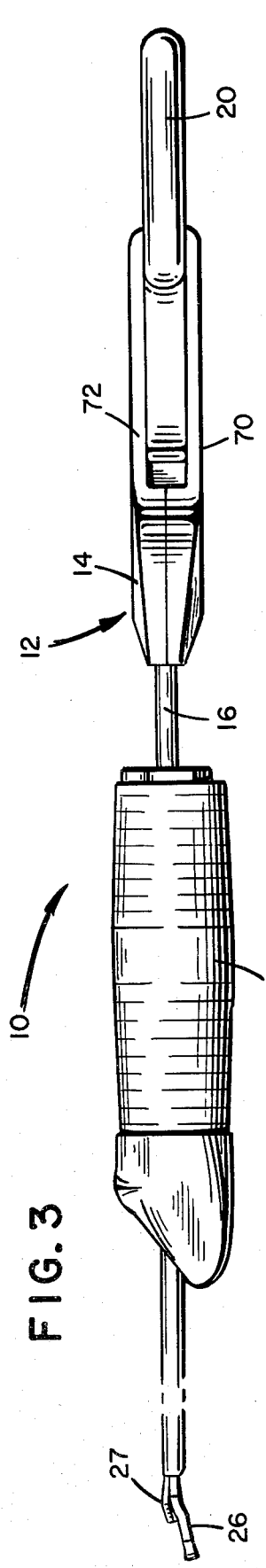
FIG. 3 is a side elevation of the clip applier.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

With reference to the drawings, in general, and to FIGS. 1 through 4, in particular, a surgical clip applier embodying the teachings of the subject invention is generally designated as 10. With reference to its orientation in FIG. 1, the clip applier comprises a housing 12 which contains a plastic body portion 14 and a forwardly extending elongated metal sleeve portion 16. The body portion 14 terminates at its rear end in an elongated projection 18. As used herein, the term "plastic" refers to those known plastics which withstand one or more conventional sterilization procedures; one such material is polysulfone.

Positioned within the housing, in the manner to be described hereinafter, are a pair of ring handles 20 and 21. Slidably mounted on the sleeve portion 16 is a cartridge assembly, or clip magazine 22. Slidably mounted within the sleeve portion 16 and the body portion 14 is an elongated jaw blade 24 which terminates at its forward end in a pair of opposed clinching jaws 26 resiliently spaced apart.

Figure 2:
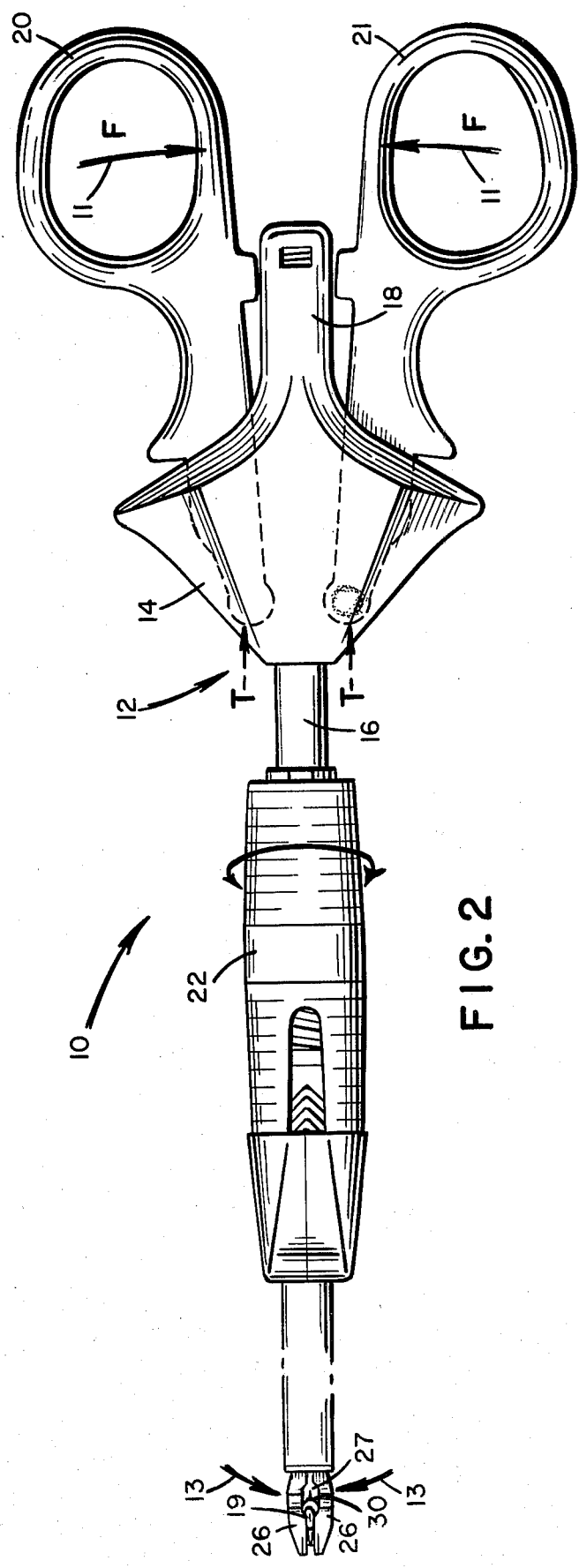
FIG. 2 is a bottom plan view of the clip applier.
Figure 12:
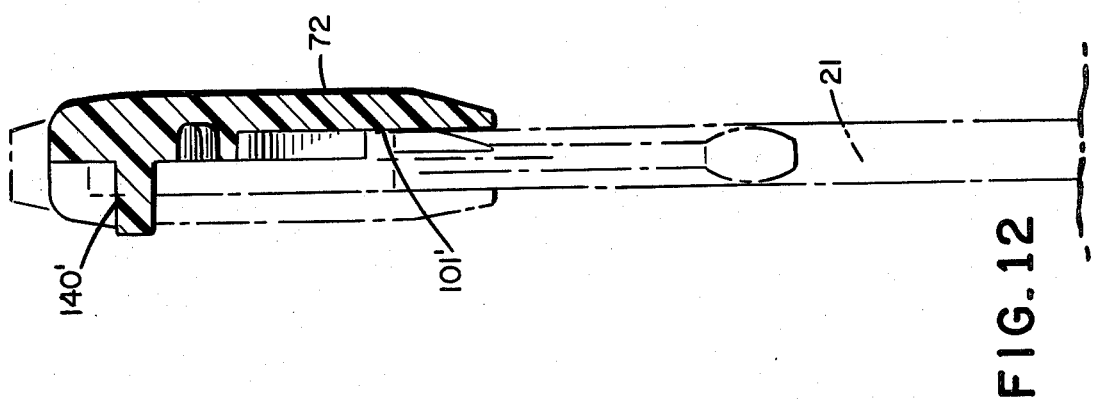
FIG. 12 is a longitudinal section taken along line 12—12 of FIG. 9.
Figure 11:
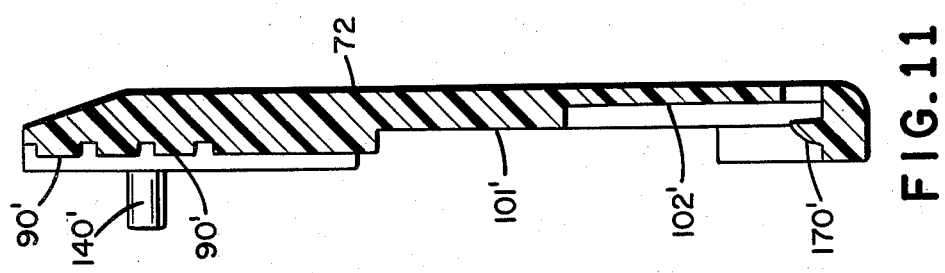
FIG. 11 is a longitudinal section taken along line 11—11 of FIG. 9.
Figure 9:
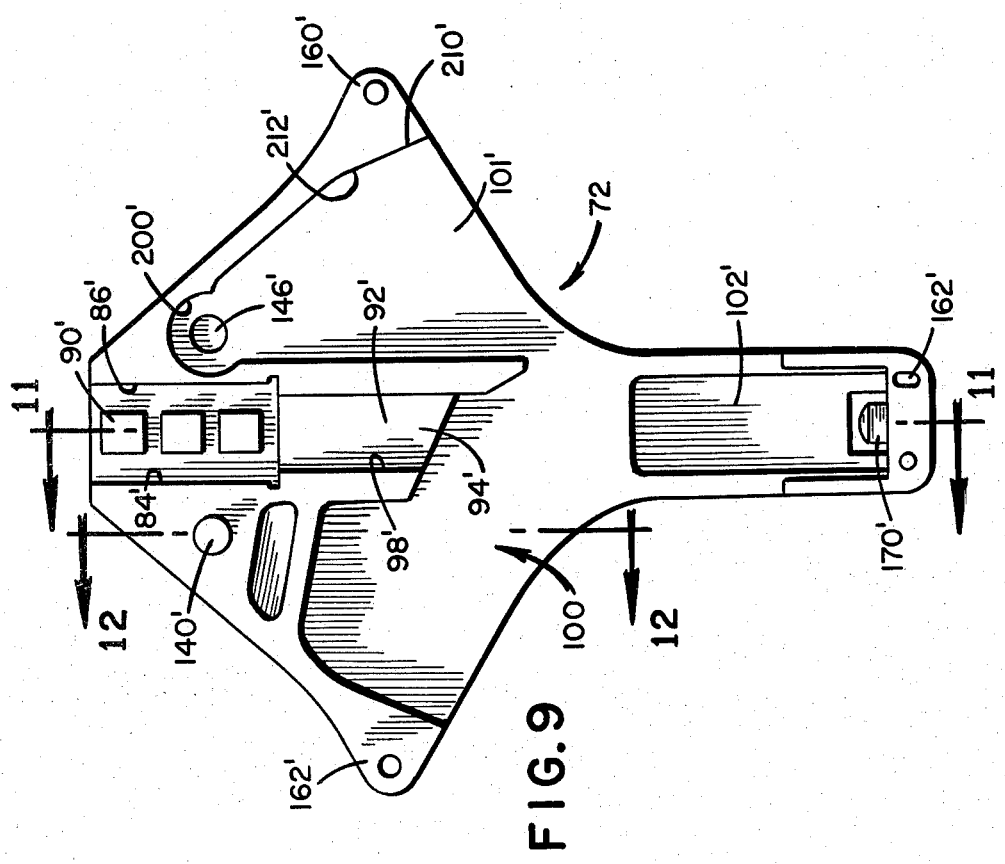
FIG. 9 is a plan view of the inside of the top body part.
Figure 10:
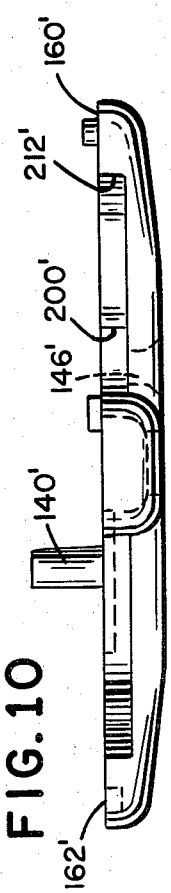
FIG. 10 is a rear view of the body part shown in FIG. 9.

Briefly, the instrument 10 is actuated by closing the handles 20, 21 together in the manner illustrated by the arrows 11 in FIG. 2. The closing of the handles serves to draw the jaw blade 24 further into the housing 12 to effect the closing of the jaws 26 in the direction illustrated by the arrows 13 in FIG. 2. The closing of the jaws 26 causes a clinching of a surgical clip 30 held between the jaws.

The cartridge assembly 22 is slidably mounted or carried on the sleeve portion 16. It may be noted that the action of the cartridge assembly 22 and its structure is described in detail in the aforementioned U.S. Pat. No. 4,152,920 and copending U.S. patent application Ser. No. 905,030, both of which are incorporated by reference herein. For purposes of this disclosure, it may be simply stated that the cartridge assembly 22 is carried on the sleeve 16 and is free to slide back and forth along the sleeve in the manner illustrated by the arrows 15 in FIG. 1 to quickly and successively accomplish the insertion of the clip 30 between the clinching jaws 26 preparatory to application of the clip during an operating procedure.

Mounted on the jaw blade 24 near the opposed jaws 26 is a clip stop 27, which prevents the clip 30 from moving rearwardly as it is applied to a blood vessel 19 or other body tissue. The specific details of the clip stop are presented in the aforementioned U.S. patent application Ser. No. 905,030.

As best seen in FIGS. 15, 16 and 19 the sleeve 16, which is part of the housing 12, is made from an elongated wrap that is formed, typically, from flat steel stock into a box 32 with edges 34 and 36 left spaced apart to define a slot 38. The rearward portion of the sleeve, as viewed in FIG. 15, contains three apertures 40 which are arranged in a longitudinal series along a bottom portion 35 of the sleeve 16. As will be explained in greater detail hereinafter, these apertures mate with projections contained in the body portion 14 to secure the sleeve portion to the body portion. Spaced forward of apertures 40 and defined on the bottom portion 35 of the sleeve 16, is an embossed projection 42, which serves as a stop for the slidable cartridge assembly 22. Positioned ahead of projection 42 is an inwardly projecting tab 33 which acts as a stroke stop.

With reference now to FIGS. 13 and 14, the jaw blade 24, which is typically made from stainless steel, is fabricated with the pair of opposed clinching jaws 26 at one end by means of slot 62 defining legs 64 and 66. The jaws 26 are bent out of the plane of the jaw blade 24 as indicated at 70 defining an angle of approximately 160°. A detailed description of the clinching jaws 24 is provided in U.S. Pat. No. 4,152,920, issued May 8, 1979, and copending application Ser. No. 905,030, referred hereinbefore.

The jaw blade 25 contains a rectangularly-shaped slot 41 which, as shown in FIGS. 6 and 7, cooperates with the tab 33 to establish a stroke stop when the tab contacts the end 43 of slot 41 that is proximal to jaws 26.

With reference to FIGS. 5 through 12, the body portion 14 of the clip applier 10 is formed from a twopiece plastic unit consisting of two identical body parts 70 and 72. It should be noted that identical body parts are used to enhance the simplicity of the device and also to reduce manufacturing cost. It is contemplated that the body portion 14 may be defined by any number of similarly or differently configured body parts without departing from the spirit and scope of the present invention.

In describing the body parts 70 and 72, like numbers, denote like elements in each part, except that the numbers associated with body part 72 are primed to facilitate the explanation of how the body parts relate to each other and how they in turn relate to the other elements constituting the clip applier. As viewed in FIGS. 5 through 9, body parts 70 and 72 resemble the shape of a stingray. It should be noted that this shape was chosen for its appearance and that numerous other shapes, readily apparent to those skilled in the art, could be used without departing from the teachings of the subject invention.

Again with reference to FIGS. 5 through 9, a sleeve-receiving trough 80 is defined at the front of the body part 70 by a bed 82, two side walls 84 and 86, and a rear wall 88. Positioned within the trough and emerging from the bed 82, are three longitudinally-spaced projections 90, which are square shaped, although other shapes are contemplated. The trough 80 is dimensioned to receive the sleeve 16 with the projections 90 mating with the apertures 40 to provide a convenient means for mounting the sleeve 16 to body part 70. The three projections 90 and rear wall 88 share in distributing the substantial thrust load which plastic body half 70 exerts against metal sleeve 16. When assembled, the projections 90' of body part 72 are received in the space 38 of sleeve 16.

Adjacent to the rear end of the trough 80 is a longitudinally-extending channel 92 that is defined by floor 94 and sidewalls 96 and 98. The top of wall 88 of trough 80 is coextensive with the floor 94 to provide a clear passageway throughout the length of the channel 92. The bed 82 of trough 80 and the floor 94 of channel 92 are in a stepped relationship so that when sleeve 16 is mounted in trough 80, a smooth passageway is provided along the entire length of the bottom portion 35 of the sleeve 16 and the floor 94 of the channel 92. The height of the projections 90 is chosen so as not to interfere with the smooth passageway.

As stated hereinbefore, the jaw blade 24 is slidably mounted within the sleeve 16. When the sleeve 16 is mounted in the trough 80, the rearward portion of the jaw blade 24 rests in the channel 92, which acts as a guide to confine the jaw blade to longitudinal movement within the body portion 14. Body part 70 contains an area 100 which is configured to provide room within the housing 12 for the remaining parts of the clip applier.

The rear end of the jaw blade 24, when positioned in channel 92, extends over a portion of a rectangular depression 102 defined in the rearward segment of body part 70. Depression 102 is configured to receive a part of a compression spring 104 that has one end abutting against wall 106 of body part 70, and the other end abutting against a pair of tapered edges 65 of the jaw blade 24. Spring 104 urges the jaw blade 24 in a forward direction out of the housing 12.

Mounted within the housing are two ring handles or levers 20 and 21, each of which has the same structure. With reference to FIGS. 1 and 5, each ring handle 20 and 21 comprises a finger ring 110 and a shank 112. The shank 112 has a generally planar bottom surface 114 and a generally planar top surface 116. Each of the ring handles is further defined by an edge 127. When the handles are mounted on body portion 14, the edges 127 oppose each other with the elongated projection 18 of body 14 being disposed therebetween.

At the free end of shank 112, a portion of top surface 116 is cut out to define a mounting member 118 which terminates in a knob-like projection 120. The wall surface 122 of the projection 120 is a cylinder and is perpendicular to the plane defined by either the top or bottom surface of the shank 112. Concentric with wall 122 of projection 120 is an aperture 124.

Along edge 127, near the mounting member 118 of each handle, the top portion 116 of the shank 112 contains a further cutout or socket-like portion 126 which is defined, in part, by substantially planar surface 128. Associated with the cutout 126 is a metal link 130, the purpose of which will be described hereinafter. Suffice it to say at this point, link 130 contains an aperture 132 that receives a projection 134 emerging from planar surface 128 in order to facilitate the placement of the end of link 130 onto planar surface 128. It is to be emphasized that the projection 134 serves to retain link 130 and is not a pivot point for the link 130.

The cutout 126 is further defined by a curved wall 136, configured in part to conform to and press against the cylindrical peripheral edge of the end of link 130 in the manner of a hinge when the link is positioned on planar surface 128. As will be explained in more detail hereinafter, the entire surface of wall 136 is substantially perpendicular to a plane defined by the arcuate movement of one of handles 20 and 21.

One of the handles, for example handle 20, is positioned on part 70 so that the aperture 124 of the handle receives a projection pin 140 formed on body part 70. When positioned in this manner, surface 116 of handle 20 is pressed against surface 101 which defines in part, the depressed area 100 of body part 70. A metal, generally L-shaped link 131 has one of its ends positioned in the cutout 126 and resting on the planar surface 128 of handle 20. In order to prevent the line 131 from moving out of cutout 126, the link contains an aperture 133 that receives projection 134, which emerges from planar surface 128. In this way the link 131 is held within the space defined between the surface 128 of handle 20 and the flat surface 101 of body part 70.

Handle 21 is positioned in body part 70 so that surface 114 of handle 21 is in contact with surface 101 of body part 70. Surface 101 is configured so that the placement of handle 21 onto surface 101 allows registry of the aperture 124 contained at the end of handle 21 with aperture 146 contained within body part 70. As described hereinafter, one end of link 130 is positioned within the open space 126 on handle 21.

As viewed in FIG. 5, the free end of link 131 is positioned below jaw blade 24, while the free end of link 130 is above jaw blade 24, so that apertures 148 and 146 of links 131 and 130, respectively, are in registry with the aperture 150 contained at the rear end of jaw blade 24. A metal pin 152 is inserted through the three registered apertures in order to allow these parts to operatively communicate with each other. The pin 152 is free to move within the body 14 since the ends 154 of pin 152 merely rest on surfaces 102 and 102'.

Body parts 70 and 72 are sandwiched together to complete the housing structure. To aid in aligning the body parts when they are placed together, registry pins 160 and registry apertures 162 are provided at the rearward portions and at the extreme ends of the midpoints of each of the body parts. Further, during assembly, pin 140 emerges through aperture 146', and appears at the exterior of body part 72, while pin 140' emerges through aperture 146 and appears from the outer surface of body part 70. These pins are hot-staked to secure the body parts together. In addition, each body part, at its rear end, is supplied with a projection 170 that is received within spring 104, the dimensions of each projection 170 and the inner diameter of the spring 104 being such that this arrangement secures the rear end of the housing.

With reference to FIGS. 1, 2, 6, 7, 17 and 18, the operating relationship between the various elements constituting the inventive clip applier will now be described in detail. With the clip 30 held between clinching jaws 26 as shown in FIG. 1, the surgeon grasps the ring handles 20 & 21 and draws them towards each other in the direction shown by the arrows 11 in FIG. 2. This drawing together of the finger rings causes a force to be transmitted to the shank portion of each handle.

The handles 20 and 21 do not rely on the pins 140, 140' of the body portion 14 in order to move arcuately within the housing 12. In fact, no stresses at all are placed on pins 140, 140' during the pivoting of the handles within the housing. Instead, the cylindrical surfaces 122 press up against mating surfaces 200 contained in each of the body parts 70 and 72. In terms of relative motion, the handles actually pivot about the cylindrical surfaces 122.

In the above manner the substantial compressive forces at the bearing surfaces 122 and 136 of the plastic handles 20 and 21 are distributed over a larger area than would be afforded by pins 134 and 140, were they to be used as pivots.

With reference to FIG. 7, the mechanical toggle arrangement of handles 20 and 21, links 130 and 131, the centers of rotation in body parts 70 and 72, and the location of pin 152 in jaw 24, all cooperate so that the inventive device permits a squeeze force F at the ring handles of about 10 lbs to generate a thrust force T of about 100 lbs acting on the jaw blade 24.

Surface 122 rotating against surface 200 can be described as a cylinder in a socket type of bearing or hinge, similarly for surface 202 against surface 136.

It is to be emphasized that the pins 140 and 140' perform only two functions: the first is to act as a means for securing the body parts together, and the second is to retain the handles within the housing when the handles are in the relaxed position.

The arcuate movement of the handles towards each other as they pivot within the housing defines a first plane. As the handles move towards each other, they each impart a force by way of surface 136 to a cylindrical peripheral portion 202 of each of the links 130 & 131. The links, in response to the force applied by each of the handles, move to define a second and third plane, respectively. Typically, the second and third planes are parallel to the first plane defined by the arcuate movement of the handles. The forces applied to the links are transmitted to the jaw blade by way of the pin 152. The jaw blade responds by being drawn into the housing, thereby compressing the spring 104. As the jaw blade is drawn into the housing as shown in FIG. 18, the inclined portions 204 and 206 of the jaw blade 24 ride against the forward edges 208 and 210 of the sleeve 16.

As the inclined edges 204 and 206 are pulled into the sleeve 16 by the action of moving the handles towards each other, the jaws 26 are drawn towards each other to accomplish a clinching of the clip 30 disposed between the jaws. When the handles are released, the compression spring urges the jaw blade in a direction out of the housing. As this takes place, the links respond to the movement of the jaw blade by causing the handles to separate from each other. Each of the handles contains a surface 210 which abuts up against a stop surface 212 contained in the body 14 in order to limit the return motion of the handles. The squeezing motion of the handle is limited by a stop member 214 contained on each of the handles. The stop members 214 abut up against the sides of the rear projection 18 of the body 14, in order to limit the deflection of the handles which might be caused by an operator squeezing in excess of the force required to close the clip 30.

The cartridge assembly 22 is received on sleeve or wrap 16 and is slidably arranged relative thereto. The assembly 22 contains a stack of clips and is arranged to coact with the jaw blade 24, clip stop 27 and jaws 26, when properly manipulated, to present its stack of clips one at a time to the jaws 26. The details of the cartridge housing assembly 22 is described in the previously mentioned U.S. Pat. No. 4,152,920 and the U.S. patent application Ser. No. 905,030.

Although the present invention has been shown and described in terms of a specific preferred embodiment, it will be appreciated by those skilled in the art that changes or modifications are possible which do not depart from the inventive concepts described and taught herein. Such changes and modifications are deemed to fall within the perview of these inventive concepts.

What is claimed is:

1. A device for applying a surgical clip, said device comprising:
   a housing;
   a pair of opposed jaws resiliently spaced apart and extending out of said housing;
   handle means, including an elongated shank terminating at one end in a manual force-receiving portion and at the other end in a mounting portion;
   mounting means in said housing, receiving said mounting portion of said shank, for mounting said shank for arcuate movement, the movement of said shank being confined to a first plane;
   a force-imparting surface defined by a first peripheral-edge portion on said shank of said handle means, said force-imparting surface being substantially perpendicular to said first plane and defining a socket;
   actuating means including a link movably mounted in said housing, said link being positioned in said socket and having a second peripheral-edge portion in contact with said force-imparting surface in the manner of a hinge for translating movement of said handle means into movement of said actuating means;
   link retaining means for holding said link within said socket; and
   means responsive to the movement of said actuating means for closing said jaws together and thereby deformably applying said surgical clip.

2. The device of claim 1, further comprising cartridge housing means, movably mounted on said housing, adapted to contain a plurality of said surgical clips, and feed them singly to a predetermined position relative to said jaws so that movement of said cartridge housing means relative to said housing will transfer a clip in said predetermined position to said jaws properly oriented to be deformend by said jaws.

3. The device of claim 1, wherein
said handle means further comprises another elongated shank terminating at one end in another manual force receiving portion and at the other end in another mounting portion;
said device further comprises another mounting means in said housing, receiving said another mounting portion for mounting said another shank for arcuate movement, the movement of said another shank being confined to said first plane, and another force-imparting surface defined on said another shank, said another force-imparting surface being substantially perpendicular to said first plane; and
said actuating means further comprises another link movably mounted in said housing, said another link having another peripheral edge portion in contact with said another force-imparting surface.

4. The device of claim 3, wherein said shank and said another shank are of precisely the same structure.

5. The device of claim 1, wherein said housing comprises first and second mating body parts of precisely the same structure.

6. The device of claim 1, wherein said mounting portion comprises a mounting member which terminates in a knob-like projection that has a curved wall, the surface of which is substantially perpendicular to said first plane, and said mounting means comprises a wall shaped to conform to said curved wall, for mounting said mounting member, said wall and said curved wall defining a pivotal connection between said housing and said shank during the arcuate movement of said shank.

7. A device for applying a surgical clip, said device comprising:
a housing;
a pair of opposed jaws resiliently spaced apart and extending out of said housing;
jaw closing means, including an elongated blade member movably mounted in said housing, for closing said jaws together, the movement of said blade member being confined to a first plane;
handle means including an elongated shank terminating at one end in a manual force-receiving portion and at the other end in a mounting portion;
mounting means in said housing, receiving said mounting portion of said shank, for mounting said shank for arcuate movement, the movement of said shank being confined to a second plane;
a force-imparting surface defined as a first peripheral-edge portion on said shank of said handle means, said force-imparting surface being substantially perpendicular to said second plane and defining a socket; and
connecting means operatively associated with said shank and said blade member, for translating the movement of said handle means into movement of said jaw closing means, said connecting means including a second peripheral-edge portion defining a force-receiving surface which is substantially perpendicular to said first plane and which is positioned in said socket, said force-imparting surface of said shank bearing against said force-receiving surface in the manner of a hinge to facilitate movement of said jaw closing means when said handle means is moved and thereby deformably applying said surgical clip;
retaining means for holding said second peripheral-edge within said socket.

8. The device of claim 7, wherein said first and second planes are substantially parallel to each other.

9. The device of claim 7, further comprising cartridge housing means, movably mounted on said housing, adapted to contain a plurality of said surgical clips and feed them singly to a predetermined position relative to said jaws so that movement of said cartridge housing means, relative to said housing, will transfer a clip in said predetermined position to said jaws properly oriented to be deformed by said jaws.

10. The device of claim 7, wherein said handle means further comprises another elongated shank terminating at one end in another manual force receiving portion and at the other end in another mounting portion;
said device further comprises another mounting means in said housing, receiving said another mounting portion for mounting said another shank for arcuate movement, the movement of said another shank being confined to a third plane, and another force-imparting surface defined on said another shank, said another force-imparting surface being substantially perpendicular to said third plane; and
said connecting means further comprises another peripheral edge portion defining another force-receiving surface which is substantially perpendicular to said first plane, said another force-imparting surface of said another shank bearing against said another force-receiving surface to facilitate movement of said jaw closing means when said handle means is moved.

11. The device of claim 10, wherein said shank and said another shank are of precisely the same structure.

12. The device of claim 10, wherein said first, second and third planes are all parallel to each other.

13. The device of claim 7, wherein said housing comprises first and second mating body parts of precisely the same structure.

14. The device of claim 7, wherein said mounting portion comprises a mounting member which terminates in a knob-like projection that has a curved wall, the surface of which is substantially perpendicular to said second plane, and said mounting means comprises a wall shaped to conform to said curved wall, for mounting said mounting member, said wall and said curved wall defining a pivotal connection between said housing and said shank during the arcuate movement of said shank.

15. The device of claim 7, wherein said first and second planes are parallel to each other.

16. A device for applying a surgical clip, said device comprising:
handle means including an elongated shank adapted for arcuate movement in response to a manually applied force, the movement of said shank being confined to a first plane, said shank terminating at one end in a knob-like projection that has a peripheral surface defining a curved wall, said peripheral surface being substantially perpendicular to said first plane;
a housing;
mounting means within said housing for receiving said projection and mounting said shank for arcuate movement in said first plane, said mounting means having a wall, the surface of which mates with said curved wall to define a socket for receiving said knob-like projection, said wall and said curved wall defining a hinge connection between said housing and said shank during the arcuate movement of said shank;

retaining means for holding said curved wall within said socket;

a pair of jaws resiliently spaced apart and extending out of said housing for receiving the surgical clip; and driving means responsive to the movement of said handle means for closing said jaws together to effect a deformation of the surgical clip.

17. A surgical instrument in which a member is mounted in a housing for rectilinear movement, the movement of said member accomplishing a desired result, said instrument comprising:

handle means including an elongated shank terminating at one end in a manual force-receiving portion and at the other end in a mounting portion;

mounting means in said housing, receiving said mounting portion of said shank, for mounting said shank for arcuate movement, the movement of said shank being confined to a first plane;

at least one force-imparting surface defined by a first peripheral-edge portion on said shank of said handle means, said force-imparting surface being substantially perpendicular to said first plane and defining a socket;

connecting means including a link positioned in said socket and having a second peripheral-edge portion defining a force-receiving surface that is substantially perpendicular to said first plane, said force-receiving surface responding to a bearing force exerted by said force-imparting surface in the manner of a hinge for translating the movement of said shank of said handle means into rectilinear movement of said member;

retaining means for holding said second peripheral-edge within said socket; and wherein said desired result comprises deforming a surgical clip.

18. The device of claim 17, wherein said handle means further comprises another elongated shank terminating at one end in another manual force receiving portion and at the other end in another mounting portion;

said device further comprises another mounting means in said housing, receiving said another mounting portion for mounting said another shank for arcuate movement, the movement of said another shank being confined to a second plane, and another force-imparting surface defined on said another shank, said another force-imparting surface being substantially perpendicular to said second plane; and said connecting means further comprises another link having another peripheral-edge portion defining another force-receiving surface that is substantially perpendicular to said second plane, said another force-receiving surface responding to a bearing force exerted by said another force-imparting surface for translating the movement of said another shank of said handle means into rectilinear movement of said member.

19. The device of claim 18, wherein said first and second planes are parallel to each other.

20. The device of claim 18, wherein said first and second planes constitute the same plane.

21. A device for applying a clip, said device comprising:

a housing;

handle means including an elongated shank terminating at one end in a manual force-receiving portion and at the other end in a mounting portion;

mounting means in said housing; receiving said mounting portion of said shank, for mounting said shank for arcuate movement, the movement of said shank being confined to a first plane;

a force-imparting surface defined by a first peripheral-edge portion on said shank of said handle means, said force-imparting surface being substantially perpendicular to said first plane and defining a socket; and clip-deforming means between which said clip is placed, said clip-deforming means including a link positioned within said socket having a second peripheral-edge surface in contact with and responsive to said force-imparting surface in the manner of a hinge to activate said clip-deforming means for deforming said clip held therebetween;

retaining means for holding said second peripheral-edge within said socket.

22. The device of claim 21, wherein said handle means further comprises another elongated shank terminating at one end in another manual force receiving portion and at the other end in another mounting portion;

said device further comprises another mounting means in said housing, receiving said another mounting portion for mounting said another shank for arcuate movement, the movement of said another shank being confined to a second plane;

another force-imparting surface defined on said another shank, said another force-imparting surface being substantially perpendicular to said second plane; and said clip-deforming means further comprises another link, said another link having another peripheral edge surface in contact with and responsive to said another force-imparting surface to activate said clip-deforming means for deforming said clip held therebetween.

23. The device of claim 22, wherein said first and second planes are parallel to each other.

24. The device of claim 22, wherein said first and second planes constitute the same plane.

25. A surgical instrument in which a member is mounted in a housing for bi-directional movement in one direction and the opposite, said instrument comprising:

first and second ring handle levers;

mounting means for mounting said first and second ring handle levers in said housing for arcuate movement;

a first link operatively associated with said first ring handle lever;

a second link operatively associated with said second ring handle lever;

means for connecting said first and second links to said member to create two opposed toggle linkages to accomplish bi-directional motion of said member in response to arcuate movement of said first and second ring handle levers;

a first cylinder-in-socket hinge operatively associated said first ring handle lever with said first link, the cylinder portion of said first hinge being defined by a peripheral-edge portion of said first link and the socket portion of said first ring defined by a peripheral-edge portion of said first ring handle; and a second cylinder-in-socket hinge operatively associating said second ring handle lever with said second link, the cylinder portion of said second hinge being defined by a peripheral-edge portion of said second link and the socket portion of said second hinge being defined by said second ring handle;

retaining means for holding said first and second cylinders within their respective sockets; and surgical clip deforming means operatively associated with said first and second ring handle levers.

26. The surgical instrument of claim 25, wherein said mounting means comprises a third cylinder-in-socket hinge operatively associating said first ring handle lever with said housing, the cylinder portion of said third hinge being defined by said first lever and the socket portion of said third hinge being defined in said housing; and a fourth cylinder-in-socket hinge operatively associating said second ring handle lever with said housing, the cylinder portion of said fourth hinge being defined by said second lever and the socket portion of said fourth hinge being defined in said housing.

* * * * *